US010940254B2

(12) United States Patent
Hacker

(10) Patent No.: US 10,940,254 B2
(45) Date of Patent: Mar. 9, 2021

(54) APPARATUS FOR EXTRACORPOREAL BLOOD TREATMENT, AND METHOD FOR OPERATING AN APPARATUS FOR EXTRACORPOREAL BLOOD TREATMENT

(71) Applicant: FRESENIUS MEDICAL CARE DEUTSCHLAND GMBH, Bad Homburg (DE)

(72) Inventor: Jurgen Hacker, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 176 days.

(21) Appl. No.: 16/076,329

(22) PCT Filed: Jan. 4, 2017

(86) PCT No.: PCT/EP2017/050155
§ 371 (c)(1),
(2) Date: Aug. 8, 2018

(87) PCT Pub. No.: WO2017/137178
PCT Pub. Date: Aug. 17, 2017

(65) Prior Publication Data
US 2019/0038823 A1 Feb. 7, 2019

(30) Foreign Application Priority Data
Feb. 10, 2016 (DE) ...................... 10 2016 001 478.4

(51) Int. Cl.
*A61M 1/16* (2006.01)

(52) U.S. Cl.
CPC ........ *A61M 1/1635* (2014.02); *A61M 1/1658* (2013.01); *A61M 1/167* (2014.02); *A61M 1/1666* (2014.02)

(58) Field of Classification Search
CPC .............. A61M 1/1635; A61M 1/1658; A61M 1/1666; A61M 1/167
See application file for complete search history.

(56) References Cited

U.S. PATENT DOCUMENTS

| 4,770,769 A * | 9/1988 | Schael ................ A61M 1/1609 |
| | | 210/96.2 |
| 2005/0131332 A1* | 6/2005 | Kelly .................. A61M 1/1633 |
| | | 604/4.01 |

(Continued)

FOREIGN PATENT DOCUMENTS

| DE | 2544258 C2 | 4/1984 |
| DE | 19929327 A1 | 12/2000 |
| WO | 2012052151 A1 | 4/2012 |

OTHER PUBLICATIONS

International Preliminary Report on Patentability issued in corresponding International Patent Application No. PCT/EP2017/050155 dated Aug. 23, 2018 (8 pages).

(Continued)

*Primary Examiner* — Krishnan S Menon
*Assistant Examiner* — Brad Gordon
(74) *Attorney, Agent, or Firm* — Kilyk & Bowersox, P.L.L.C.

(57) ABSTRACT

The invention relates to an apparatus for extracorporeal blood treatment that comprises a device 1 for providing fresh dialysate and a drain 2 for used dialysate, a balancing device 4 for balancing fresh dialysate and used dialysate, an ultrafiltration device 15, and a dialyser 3 that is divided into a blood chamber 6 and a dialysate chamber 7 by a semi-permeable membrane 5. The invention further relates to a method for operating such an apparatus for extracorporeal blood treatment. The apparatus according to the invention is based on the use of the ultrafiltration device 15 of the blood treatment apparatus for raising the liquid level in the air separation device 12 on the secondary side of the dialysate system I. In the apparatus according to the invention, the ultrafiltration device 15 is designed such that the ultrafiltration device can be operated not only in an ultrafiltration mode, but also in a ventilation mode. In the ultrafiltration (Continued)

mode, the ultrafiltration device 15 is operated in such a way that used dialysate is removed from the container 12A of the first air separation device 12 whereas in a ventilation mode the ultrafiltration device 15 is operated in the opposite direction so that used dialysate is supplied into the container 12A of the first air separation device 12, as a result of which the liquid level 12D rises in the container of the first air separation device.

15 Claims, 1 Drawing Sheet

(56) References Cited

U.S. PATENT DOCUMENTS

| | | | |
|---|---|---|---|
| 2009/0084718 A1* | 4/2009 | Prisco | A61M 1/1658 |
| | | | 210/151 |
| 2011/0120302 A1* | 5/2011 | Raiford | A61M 1/167 |
| | | | 95/19 |
| 2014/0220699 A1 | 8/2014 | Pudil et al. | |

OTHER PUBLICATIONS

International Search Report issued in corresponding International Patent Application No. PCT/EP2017/050155 (with English translation) dated Mar. 31, 2017 (6 pages).

* cited by examiner

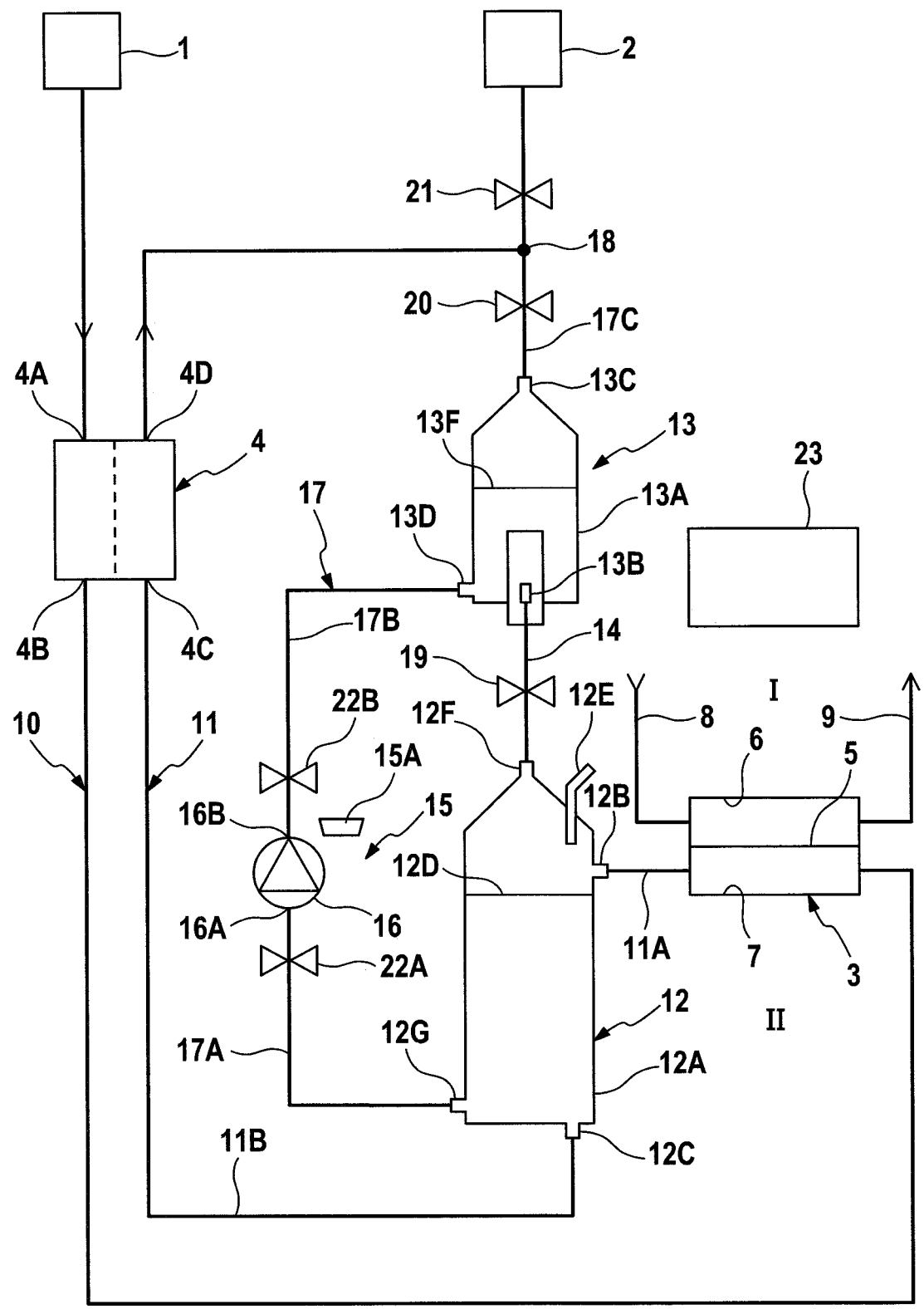

APPARATUS FOR EXTRACORPOREAL BLOOD TREATMENT, AND METHOD FOR OPERATING AN APPARATUS FOR EXTRACORPOREAL BLOOD TREATMENT

This application is a National Stage Application of PCT/EP2017/050155, filed Jan. 4, 2017, which claims priority to German Patent Application No. 10 2016 001 478.4, filed Feb. 10, 2016.

The invention relates to an apparatus for extracorporeal blood treatment that comprises a device for providing fresh dialysate and a drain for used dialysate, a balancing device for balancing fresh dialysate and used dialysate, and a dialyser that is divided into a blood chamber and a dialysate chamber by a semi-permeable membrane. The invention further relates to a method for operating such an apparatus for extracorporeal blood treatment.

The known extracorporeal blood treatment apparatuses comprise an extracorporeal blood circuit, which includes the blood chamber of a dialyser, and a dialysate system, which includes the dialysate chamber of a dialyser. The blood circuit and dialysate system are separated by the semi-permeable membrane of the dialyser. In the dialysate system, fresh dialysate flows into the dialysate chamber from a device for providing fresh dialysate, whilst used dialysate flows out of the dialysate chamber into the drain. To balance fresh and used dialysate, the known blood treatment apparatuses have a balancing device. In addition, the known blood treatment apparatuses generally comprise an ultrafiltration device, by which a predetermined volume of dialysate can be extracted from the dialysate system. Since the balancing device ensures that the volume of the fresh dialysate is the same as the used dialysate, ultrafiltrate is extracted from the patient via the semi-permeable membrane during operation of the ultrafiltration device.

The part of the dialysate system in which fresh dialysate flows into the dialysate chamber via a dialysate supply line will be referred to as the primary side hereinafter, and the part of the dialysate system in which used dialysate flows into the drain via a dialysate discharge line will be denoted the secondary side. Blood treatment apparatuses are known that have an air separation device on both the primary and secondary side of the dialysate system, which devices comprise a container having one inlet for fresh dialysate and one for used dialysate, and one outlet for fresh dialysate and one for used dialysate. The inlet and outlet are arranged such that a liquid level that can rise or fall forms in the container. The separated air collects in the container above the liquid level. These air separation devices ensure that the hydraulic system of the blood treatment apparatus is ventilated.

On the secondary side, the air separation device is arranged upstream of the balancing device immediately before the branch at which the ultrafiltrate is extracted from the dialysate system. When ultrafiltrate is extracted from the dialysate system, the liquid level can drop owing to the accumulation of air in the container of the air separation device. If the level drops below a predetermined level, the level in the container has to be raised again by discharging air.

For correct balancing, it has to be borne in mind during operation of the blood treatment apparatus that the air collecting in the container of the air separation device during the blood treatment can change the liquid balance by the corresponding volume.

Blood treatment apparatuses are known which have an additional connecting line to the air separation device on the primary side for raising the level in the air separation device on the secondary side, so that fresh dialysate can be supplied to the container of the air separation device on the secondary side in order to raise the liquid level. However, the fluid connection between the primary and secondary side proves disadvantageous in these blood treatment apparatuses since it can lead to fresh dialysate being contaminated with used dialysate. Other blood treatment apparatuses have an additional pump for supplying dialysate into the container of the air separation device, which pump is arranged in the drain line leading to the outflow. The drawback is that an additional component is required, which also leads to increased maintenance requirements.

The problem addressed by the invention is that of providing an apparatus for extracorporeal blood treatment that makes ventilation possible on the secondary side of the dialysate system. More particularly, the problem addressed by the invention is that of creating an extracorporeal blood treatment apparatus in which the primary and second side of the dialysate system are separate from one another and which has a simplified design. It is also an object of the invention to disclose a method for operating an extracorporeal blood treatment apparatus, by which the secondary side of the dialysate system can be ventilated without the use of additional components and without the risk of fresh dialysate being contaminated with used dialysate.

These objects are achieved according to the invention by the features of the independent claims. The dependent claims relate to advantageous embodiments of the invention.

The apparatus for extracorporeal blood treatment according to the invention has an ultrafiltration device for removing used dialysate from the dialysate system and supplying the used dialysate to the outlet while bypassing the balancing device. An ultrafiltration device of this type is part of the prior art. The ultrafiltration device is in fluid communication with the container of an air separation device arranged on the secondary side of the dialysate system. Therefore, dialysate is removed from the container during operation of the ultrafiltration device, as a result of which the liquid level in the container drops. The ultrafiltration device can remove liquid from the container of the air separation device directly, or can be connected to a line leading to the container or leading from the container.

The apparatus according to the invention is based on the use of the ultrafiltration device of the blood treatment apparatus for raising the liquid level in the air separation device on the secondary side of the dialysate system.

In the apparatus according to the invention, the ultrafiltration device is designed such that the ultrafiltration device can be operated not only in an ultrafiltration mode, but also in a ventilation mode. As a result, the ultrafiltration device fulfils two different roles. In the ultrafiltration mode, the ultrafiltration device is operated such that used dialysate is removed from the container of the air separation device. In the ventilation mode on the other hand, the ultrafiltration device is operated in the opposite direction, and so used dialysate is supplied to the container of the air separation device, as a result of which the liquid level in the container of the first air separation device rises. As the liquid level rises, the air in the container is displaced.

Omitting additional components simplifies the design and reduces the maintenance requirements of the blood treatment apparatus by comparison with the known blood treatment apparatuses. Reducing the number of components also makes it easier to clean the dialysate system. Moreover, the primary and secondary side of the dialysate system remain separate from one another, and so there is no risk of fresh dialysate becoming contaminated with used dialysate as a result of the connection between the primary and secondary side of the dialysate system. The lack of a connection between the primary and secondary side also prevents the two parts of the dialysate system from influencing one another owing to pressure fluctuations when the liquid level rises in the respective air separation devices.

Another advantage of the apparatus according to the invention is the precise balancing of the patient during the extracorporeal blood treatment, since the blood treatment apparatus makes it possible to replace the air in the container of the air separation device with liquid in a volume-controlled manner, and so any errors that occur because of the accumulation of air in the container are corrected during the balancing.

A preferred embodiment of the invention provides a second air separation device, which comprises a container that is in fluid communication with the first air separation device and the ultrafiltration device in such a way that the air discharged from the first air separation device in the ventilation mode when the fluid level rises is collected in the container of the second air separation device, whilst the ultrafiltration device is operated in the opposite direction to supply used dialysate into the container of the first air separation device. The second air separation device ensures that the ultrafiltration device cannot take in air in the ventilation mode. The ultrafiltration device can remove the used dialysate from the container of the second air separation device provided that the container of the second air separation device is filled with dialysate, i.e. the liquid level in the container of the second air separation device has not dropped below a predetermined value.

In another preferred embodiment, the blood treatment apparatus comprises a control unit which is designed such that the ultrafiltration device is operated alternately in the ultrafiltration mode and in the ventilation mode. The preferred embodiment can also provide a mode in which switching from the ultrafiltration mode to the ventilation mode only takes place once, and after that the treatment is continued in the ultrafiltration mode.

The control unit can be a separate control unit or a component of the central control unit of the blood treatment apparatus. While liquid is being sucked from the container of the second air separation device by the ultrafiltration device in the ventilation mode, the liquid level in the container of the second air separation device drops. By operating the ultrafiltration device in the ultrafiltration mode, the liquid level in the container of the second air separation device is raised again. Operating the ultrafiltration device alternately in the ultrafiltration and ventilation modes makes it possible to deliver smaller volumes of liquid, and so it is ensured that the container of the first air separation device is always sufficiently full of liquid.

In another preferred embodiment, the control unit is designed such that the ultrafiltration device is operated in the ultrafiltration mode for a predetermined first period of time and in the ventilation mode for a predetermined second period of time. The periods of time can be such that a predetermined volume of liquid is delivered during each one.

To monitor the liquid level, the first air separation device preferably comprises a level indicator, the control unit being designed such that the ultrafiltration device is operated alternately in the ultrafiltration mode and the ventilation mode until the level indicator measures a predetermined level.

In a particularly preferred embodiment, the container of the first air separation device comprises a ventilation port for discharging air and an ultrafiltration port for supplying or discharging used dialysate, the ventilation port being arranged above the ultrafiltration port so that used dialysate can be supplied to the container below the liquid level or removed from the container. The container of the second air separation device preferably comprises an inlet and an outlet, the inlet being arranged below the outlet, and preferably comprises an ultrafiltration port for supplying or discharging used dialysate, which port is arranged below the outlet so that used dialysate can be supplied to the container below the liquid level or removed from the container.

The ultrafiltration device preferably comprises an ultrafiltration pump having a first and a second port, the first port being connected to the ultrafiltration port of the container of the first air separation device via a first portion of an ultrafiltration line and the second port being connected to the ultrafiltration port of the container of the second air separation device via a second portion of the ultrafiltration line. The ultrafiltration pump can have various designs, for example it may be an occlusive roller pump into which a hose line can be placed. The ultrafiltration pump can also be a membrane pump that additionally comprises an inlet valve and outlet valve at the inlet and outlet, respectively. To measure the amount of ultrafiltered liquid, the ultrafiltration device can have a suitable measurement device. For example, to determine the amount of fluid in the case of a roller pump the revolutions can be counted, and to determine the amount in the case of a membrane pump the pump strokes can be counted. Alternatively, the volume flow rate can be detected by a flow sensor and an evaluation unit.

The ventilation port of the container of the first air separation device is connected to the inlet to the container of the second air separation device via a ventilation line, and the outlet of the container of the second air separation device is connected to the drain via a third portion of the ultrafiltration line, a first valve being arranged in the ventilation line and a second valve being arranged in the third portion of the ultrafiltration line. By means of the valves, the fluid connections between the containers can be produced or broken.

The control unit is designed such that the first valve is closed and the second valve is open in the ultrafiltration mode. This ensures that used dialysate can be removed from the container of the first ultrafiltration device and delivered into the drain while bypassing the balancing device. In addition, the control unit is designed such that the first valve is open and the second valve is closed in the ventilation mode, and so used dialysate can be pumped out of the container of the second air separation device into the container of the first air separation device in order to raise the liquid level.

An embodiment of the invention will be described in detail below with reference to the drawing, which is a highly simplified schematic view of the dialysate system of the extracorporeal blood treatment apparatus, the ultrafiltration device being operated in an ultrafiltration mode and a ventilation mode.

The apparatus for extracorporeal blood treatment, in particular a dialysis apparatus, comprises a device 1 for providing fresh dialysate and a drain 2 for used dialysate. The drain 2 is understood to be a container for collecting used dialysate or an outflow, for example. In addition, the extracorporeal blood treatment apparatus comprises a dialyser 3 and a balancing device 4. The dialyser 3 is divided into a blood chamber 6 and a dialysate chamber 7 by a semipermeable membrane 5. An arterial blood line 8 leads to the inlet to the blood chamber 6 and a venous blood line 9 leads away from the outlet of the blood chamber 6. The arterial and venous blood lines 8, 9 and the blood chamber 6 of the dialyser 3 form the extracorporeal blood circuit I of the blood treatment apparatus. The semi-permeable membrane 5 of the dialyser 3 separates the extracorporeal blood circuit I from the dialysate system II of the blood treatment apparatus.

A dialysate supply line 10 leads to the inlet to the dialysate chamber 7 from the device 1 for providing fresh dialysate and a dialysate discharge line 11 leads to the drain 2 from the outlet of the dialysate chamber 7, and so fresh dialysate can flow through the dialysate chamber 7 into the drain 2 from the device 1 for providing fresh dialysate.

The balancing device 4 balances fresh dialysate against used dialysate. This ensures that the volume of fresh dialysate matches the volume of used dialysate. The balancing device 4 (only shown schematically in FIG. 1), which has a primary-side inlet 4A and outlet 4B for fresh dialysate and a secondary-side inlet 4C and outlet 4D for used dialysate, is connected into the dialysate supply line 10 and the dialysate discharge line 11 such that fresh dialysate flows via the primary side of the balancing device 4 and used dialysate flows via the secondary side. To balance fresh and used dialysate, the balancing device can have balancing chambers. For balancing, the volume flow rate can, however, also be monitored by flow sensors. Balancing devices can be found in the prior art in various forms.

The dialysate system II comprises a primary side and a secondary side. The primary side includes the part of the dialysate system that is upstream of the dialysate chamber, whereas the secondary side includes the part of the dialysate system II that is downstream of the dialysate chamber 7 of the dialyser 3. Air in the dialysate (air bubbles) is separated on both the primary and secondary side of the dialysate system II.

FIG. 1 only shows those components of the air separation system that are located on the secondary side of the dialysate system II. The air separation system comprises a first air separation device 12 and a second air separation device 13.

The first air separation device 12 comprises a container 12A having an inlet 12B and an outlet 12C. The inlet 12B is above the outlet 12C, which is arranged in the region of the bottom of the container 12A. The outlet of the dialysate chamber 7 of the dialyser 3 is connected to the inlet 12B of the first air separation device 12 via a first line portion 11A of the dialysate discharge line 11, whereas the outlet 12C of the first air separation device 12 is connected to the drain 2 via a second line portion 11B. The first air separation device 12 can, for example, be a conventional drip chamber of the prior art.

During operation of the blood treatment apparatus, used dialysate flows through the container 12A of the first air separation device 12, and so a liquid level 12D forms in the container 12A. To detect the liquid level in the container 12A, the first air separation device 12 comprises a level indicator 12E.

The air (air bubbles) separated by the first air separation device 12 collects in the space in the container 12A above the liquid level 12D.

The second air separation device 13, which can also be a conventional drip chamber, comprises a container 13A having an inlet 13B and an outlet 13C. The outlet 13C is arranged on the container 13A above the inlet 13B. During operation of the blood treatment apparatus, a liquid level 13F forms in the container 13A.

The container 12A of the first air separation device 12 comprises a ventilation port 12F that is arranged above the inlet and outlet 12B, 12C and is connected to the inlet 13B to the second air separation device 13 via a ventilation line 14.

In addition, the blood treatment apparatus has an ultrafiltration device 15, by which a predetermined amount of ultrafiltrate can be extracted from the patient via the semi-permeable membrane 5 of the dialyser 3. The ultrafiltration device 15 comprises an ultrafiltration pump 16 having a first port 16A and a second port 16B. The first port 16A of the ultrafiltration pump 16 is connected, via a first portion 17A of the ultrafiltration line 17, to an ultrafiltration port 12G which is arranged on the container 12A of the first air separation device 12 below the inlet 12B and the ventilation port 12F, preferably in the region of the bottom of the container 12A. The second port 16B of the ultrafiltration pump 16 is connected, via a second portion 17B of the ultrafiltration line 12, to an ultrafiltration port 13D which is provided on the container 13A of the second air separation device 13 below the outlet 13B, preferably in the region of the bottom of the container. A third portion of the ultrafiltration line 17 leads from the outlet 13C of the container 13A of the second air separation device 13 to the outflow 2. In this case, the third portion 17B of the ultrafiltration line is connected to the second line portion 11B of the dialysate discharge line 11 at a connection point 18 that is downstream of the balancing device 14.

The ultrafiltration pump 16 can be an occlusive roller pump or a membrane pump. If the ultrafiltration pump 16 is a membrane pump, an inlet valve 22A is arranged in the ultrafiltration line 17 upstream of the pump and an outlet valve 22B is arranged in the ultrafiltration line downstream of the pump. There is no need for inlet and outlet valves 22A, 22B if the ultrafiltration pump is an occlusive pump.

To break the fluid connection, a first valve 19 is provided on the ventilation line 14, a second valve 20 is provided on the third portion 17C of the ultrafiltration line 17, and a third valve 21 is provided on the portion of the second line portion 11B of the dialysate discharge line 11 downstream of the connection point 18.

The ultrafiltration device 15 also has a measurement device 15A (only shown by way of indication) for measuring the amount of ultrafiltered liquid. To determine the amount of ultrafiltered liquid in the case of a roller pump, the measurement device 15A counts the revolutions, and said device counts the membrane strokes to determine the amount of liquid in the case of a membrane pump. Alternatively, a flow sensor having an evaluation unit for measuring the amount of ultrafiltered liquid can also be provided.

The blood treatment apparatus has a central control unit 23, by which the individual components of the blood treatment apparatus are controlled. The central control unit 23 can comprise a data processing unit, on which a computer program runs. The control unit 23 controls the ultrafiltration pump 16 of the ultrafiltration device 15, the individual valves 19 to 21 and the inlet and outlet valves 22A and 22B by means of control lines (not shown).

In the following, it will be described in detail how the control unit actuates the ultrafiltration pump and the valves in order to separate air (air bubbles) in the used dialysate on the secondary side of the dialysate system II. For this purpose, the control unit 23 actuates the ultrafiltration pump and the valves in such a way that the following method steps are carried out.

First, the ultrafiltration device 15 is operated in an ultrafiltration mode. This corresponds to the normal operation of the dialysis apparatus if ultrafiltration is intended to be carried out. In the ultrafiltration mode shown in FIG. 1, the second valve 20 and the third valve 21 are open and the first valve 19 is closed. If they are actually provided, the inlet and outlet valves 22A and 22B are also open. In the ultrafiltration mode, the ultrafiltration pump 16 extracts used dialysate from the dialysate system II out of the container 12A of the first air separation device 12, which used dialysate flows into the drain 2 while bypassing the balancing device 4. The used dialysate flows through the first, second and third portion 17A to 17C of the ultrafiltration line 17 to the connection port 18, and so the dialysate can flow into the drain 2.

Air (air bubbles) in the dialysate is separated in the first air separation device 12 and collects above the liquid level 12D in the container 12A of the first air separation device 12. During operation of the ultrafiltration pump 16, the liquid level 12D in the first air separation device 12 can drop. It is therefore necessary to raise the liquid level again.

To raise the liquid level in the first air separation device 12, the control unit 23 actuates the ultrafiltration device 4 in such a way that the ultrafiltration pump 16 is operated in a ventilation mode, in which the ultrafiltration pump runs in the opposite direction, i.e. the delivery direction of the pump is reversed. In the ventilation mode, the control unit 23 opens the first valve 19 and closes the second valve 20, so the fluid connection to the drain 2 is broken. The ultrafiltration pump 16 now delivers used dialysate located in the container 13A of the second air separation device 13 into the container 12A of the first air separation device 12, and so the liquid level 12D in the first air separation device 12 rises. The ultrafiltration pump is operated for a predetermined period of time of such a length that only some of the liquid in the second air separation device 12 is delivered into the first air separation device 12. After this, the control unit 23 switches the ultrafiltration device 15 back into the ultrafiltration mode, the control unit 23 closing the first valve 19 again and re-opening the second valve 20. During operation of the ultrafiltration pump in the ultrafiltration mode, the container 13A of the second air separation device 13 is filled back up with used dialysate. The operation in ultrafiltration mode is carried out for a predetermined second period of time. The control unit actuates the ultrafiltration device 16 in such a way that the ultrafiltration device is operated alternately in the ultrafiltration mode and ventilation mode until the level indicator 12E of the first air separation device 12 detects a predetermined level, i.e. that the liquid level in the first air separation device has risen back to the predetermined level. It is also possible for switching from the ultrafiltration mode into the ventilation mode to only be carried out once, after which the treatment is continued in the ultrafiltration mode.

In the ventilation mode, the air in the container 12A of the first air separation device 12 is conducted into the second air separation device 13 via the ventilation line 14. Since this air is separated in the second air separation device, in the ventilation mode the ultrafiltration pump 16 cannot take in air that might flow between the two ventilation devices.

In the blood treatment apparatus according to the invention, the air (air bubbles) separated from the dialysate system cannot cause incorrect balancing. Replacing the accumulated air with liquid corrects the balancing error that occurs temporarily during dialysis as a result of air trapped in the volume-controlled balancing circuit.

LIST OF REFERENCE SIGNS

Device for providing fresh dialysate 1
Drain 2
Dialyser 3
Balancing device 4
Primary-side inlet to the balancing device 4A,
Primary-side outlet of the balancing device 4B,
Secondary-side inlet to the balancing device 4C
Secondary-side outlet of the balancing device 4D
Semi-permeable membrane 5
Blood chamber 6
Dialysate chamber 7
Arterial blood line 8
Venous blood line 9
Extracorporeal blood circuit I
Dialysate system II
Dialysate supply line 10
Dialysate discharge line 11
First line portion 11A of the dialysate discharge line
Second line portion 11B of the dialysate discharge line
First air separation device 12
Container 12A of the first air separation device
Inlet 12B to the first air separation device
Outlet 12C of the first air separation device
Liquid level 12D of the first air separation device
Level indicator 12E
Ventilation port 12F of the first air separation device
Ultrafiltration port 12G of the first air separation device
Second air separation device 13
Container 13A of the second air separation device 13A
Inlet 13B to the second air separation device
Outlet 13C of the second air separation device
Ultrafiltration port 13D of the second air separation device
Liquid level 13F of the second air separation device
Ventilation line 14
Ultrafiltration device 15
Measurement device 15A for measuring the amount of ultrafiltered liquid
Ultrafiltration pump 16
First port 16A of the ultrafiltration pump
Second port 16B of the ultrafiltration pump
Ultrafiltration line 17
First portion 17A of the ultrafiltration line
Second portion 17B of the ultrafiltration line
Third portion 17C of the ultrafiltration line
Connection point 18
First valve 19
Second valve 20
Third valve 21
Inlet valve and outlet valve 22A, 22B
Control unit 23

The invention claimed is:

1. Apparatus for extracorporeal blood treatment, comprising
a device for providing fresh dialysate and a drain for used dialysate,
a balancing device for balancing fresh dialysate and used dialysate,
a dialyser, which is divided into a blood chamber and a dialysate chamber by a semi-permeable membrane,
a dialysate supply line for fresh dialysate, leading from the device for providing fresh dialysate to an inlet to the dialysate chamber via the balancing device, and a dialysate discharge line for used dialysate, leading from an outlet of the dialysate chamber to the drain via the balancing device, a first air separation device comprising a container having an inlet for supplying used dialysate and an outlet for discharging used dialysate, which are arranged such that a liquid level forms in the container, the dialysate discharge line comprising a first line portion that leads from the outlet of the dialysate chamber to the inlet to the container, and comprising a second line portion that leads from the outlet of the container to the drain via the balancing device, an ultrafiltration device for removing used dialysate from the container of the first air separation device and for supplying the used dialysate to the drain through an ultrafiltration line while bypassing the balancing device, the ultrafiltration device comprising an ultrafiltration pump, wherein the ultrafiltration device is designed such that, the ultrafiltration pump is operated in an ultrafiltration mode to remove used dialysate from the container of the first air separation device and the ultrafiltration pump is operated in a ventilation mode in the opposite direction to supply used dialysate into the container of the first air separation device such that the liquid level rises in the container of the first air separation device.

2. Apparatus for extracorporeal blood treatment according to claim 1, further comprising a control unit which is designed such that the ultrafiltration device is operated alternately in the ultrafiltration mode and in the ventilation mode.

3. Apparatus for extracorporeal blood treatment according to claim 2, wherein the control unit is designed such that the ultrafiltration device is operated in the ultrafiltration mode for a predetermined first period of time and in the ventilation mode for a predetermined second period of time.

4. Apparatus for extracorporeal blood treatment according to claim 2, wherein the first air separation device comprises a level indicator, the control unit being designed such that the ultrafiltration device is operated alternately in the ultrafiltration mode and the ventilation mode until the level indicator measures a predetermined level.

5. Apparatus for extracorporeal blood treatment, comprising a device for providing fresh dialysate and a drain for used dialysate, a balancing device for balancing fresh dialysate and used dialysate, a dialyser, which is divided into a blood chamber and a dialysate chamber by a semi-permeable membrane, a dialysate supply line for fresh dialysate, leading from the device for providing fresh dialysate to an inlet to the dialysate chamber via the balancing device, and a dialysate discharge line for used dialysate, leading from an outlet of the dialysate chamber to the drain via the balancing device, a first air separation device comprising a container having an inlet for supplying used dialysate and an outlet for discharging used dialysate, which are arranged such that a liquid level forms in the container, the dialysate discharge line comprising a first line portion that leads from the outlet of the dialysate chamber to the inlet to the container, and comprising a second line portion that leads from the outlet of the container to the drain via the balancing device an ultrafiltration device for removing used dialysate from the container of the first air separation device and for supplying the used dialysate to the drain while bypassing the balancing device, wherein the ultrafiltration device is designed such that, the ultrafiltration device is operated in an ultrafiltration mode to remove used dialysate from the container of the first air separation device and the ultrafiltration device is operated in a ventilation mode in the opposite direction to supply used dialysate into the container of the first air separation device such that the liquid level rises in the container of the first air separation device, and a second air separation device comprising a container that is in fluid communication with the first air separation device and the ultrafiltration device in such a way that the air discharged from the first air separation device in the ventilation mode when the fluid level rises is collected in the container of the second air separation device, whilst the ultrafiltration device is operated in the opposite direction to supply used dialysate into the container of the first air separation device.

6. Apparatus for extracorporeal blood treatment according to claim 5, wherein the container of the first air separation device comprises a ventilation port for discharging air and an ultrafiltration port for supplying or discharging used dialysate, the ventilation port being arranged above the ultrafiltration port, and the container of the second air separation device comprises an inlet and an outlet, the inlet being arranged below the outlet, and an ultrafiltration port for supplying or discharging used dialysate, the ultrafiltration port being arranged below the outlet.

7. Apparatus for extracorporeal blood treatment according to claim 6, wherein the ultrafiltration pump has a first and a second port, the first port being connected to the ultrafiltration port of the container of the first air separation device via a first portion of the ultrafiltration line and the second port being connected to the ultrafiltration port of the container of the second air separation device via a second portion of the ultrafiltration line, and the ventilation port of the container of the first air separation device is connected to the inlet to the container of the second air separation device via a ventilation line, and the outlet of the container of the second air separation device being connected to the drain via a third portion of the ultrafiltration line, a first valve being arranged in the ventilation line and a second valve being arranged in the third portion of the ultrafiltration line.

8. Apparatus for extracorporeal blood treatment according to claim 7, wherein the control unit is designed such that the first valve is closed and the second valve is open in the ultrafiltration mode.

9. Apparatus for extracorporeal blood treatment according to claim 7, wherein the control unit is designed such that the first valve is open and the second valve is closed in the ventilation mode.

10. Method for operating an apparatus for extracorporeal blood treatment, comprising:

a device for providing fresh dialysate and a drain for used dialysate, a balancing device for balancing fresh dialysate and used dialysate, a dialyser, which is divided into a blood chamber and a dialysate chamber by a semipermeable membrane, a dialysate supply line for fresh dialysate, leading from the device for providing fresh dialysate to an inlet to the dialysate chamber via the balancing device, and a dialysate discharge line for used dialysate, leading from an outlet of the dialysate chamber to the drain via the balancing device, a first air separation device comprising a container having an inlet for supplying used dialysate and an outlet for discharging used dialysate, which are arranged such that a liquid level forms in the container, the dialysate discharge line comprising a first line portion that leads from the outlet of the dialysate chamber to the inlet to the container, and comprising a second line portion that leads from the outlet of the container to the drain via the balancing device, an ultrafiltration device for removing used dialysate from the container of the first air separation device and for supplying the used dialysate to the drain through an ultrafiltration line while bypassing the balancing device, the ultrafiltration device comprising an ultrafiltration pump, wherein the ultrafiltration device comprising an ultrafiltration pump that is operated in an ultrafiltration mode to remove used dialysate from the container of the first air separation device and operated in a ventilation mode in the opposite direction to supply used dialysate into the container of the first air separation device such that the liquid level rises in the container of the first air separation device.

11. Method according to claim 10, characterised in that air discharged from the container of the first air separation device in the ventilation mode when the liquid level rises is collected in a container of a second air separation device, whilst the ultrafiltration device is operated in the opposite direction to supply used dialysate from the container of the second air separation device into the container of the first air separation device.

12. Method according to claim 11, characterised in that the air collected in the container of the second air separation device is discharged into the drain.

13. Method according to claim 10, characterised in that the ultrafiltration device is operated alternately in the ultrafiltration mode and in the ventilation mode.

14. Method according to claim 10, characterised in that the ultrafiltration device is operated in the ultrafiltration mode for a predetermined first period of time and in the ventilation mode for a predetermined second period of time.

15. Method according to claim 10, characterised in that the ultrafiltration device is operated alternately in the ultrafiltration mode and the ventilation mode until the level in the container of the first air separation device is at a predetermined value.

* * * * *